United States Patent
Oba et al.

(10) Patent No.: US 8,201,386 B2
(45) Date of Patent: Jun. 19, 2012

(54) METHOD FOR MAKING PACKAGE-ABSORBENT ARTICLE ASSEMBLY AND PACKAGE-ABSORBENT ARTICLE ASSEMBLY OBTAINED BY THE SAME

(75) Inventors: Kenji Oba, Kagawa (JP); Keijiro Yokoe, Kagawa (JP); Michiyo Fujikawa, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 30 days.

(21) Appl. No.: 12/863,226

(22) PCT Filed: Nov. 20, 2008

(86) PCT No.: PCT/JP2008/071077
§ 371 (c)(1),
(2), (4) Date: Oct. 7, 2010

(87) PCT Pub. No.: WO2009/090795
PCT Pub. Date: Jul. 23, 2009

(65) Prior Publication Data
US 2011/0017628 A1    Jan. 27, 2011

(30) Foreign Application Priority Data
Jan. 17, 2008  (JP) .................... 2008-008530

(51) Int. Cl.
*B65B 9/06* (2006.01)
*B65H 45/09* (2006.01)
*B65H 45/22* (2006.01)
(52) U.S. Cl. ............. 53/429; 53/450; 53/117; 53/116
(58) Field of Classification Search ............ 53/460, 53/429, 416, 206, 116, 550, 450, 117
See application file for complete search history.

(56) References Cited

U.S. PATENT DOCUMENTS
4,781,293 A * 11/1988 Johns ................... 206/441
(Continued)

FOREIGN PATENT DOCUMENTS
JP       07-313547       12/1995
(Continued)

OTHER PUBLICATIONS

International Search Report from corresponding PCT/JP2008/071077, dated Dec. 22, 2008, 4 pages.

*Primary Examiner* — Rinaldi Rada
*Assistant Examiner* — Gloria R Weeks
(74) *Attorney, Agent, or Firm* — Brinks Hofer Gilson & Lione

(57) ABSTRACT

The present invention includes following the steps of:
In a first step, first and second breast milk absorbent pads 2(*i*), 3(*i*) are fed onto wrapping sheet web 29. In a second step, the first breast milk absorbent pad 2(*ii*) is fed so as to be displaced from a transverse center line 32 toward an upper end 30 by ¼ of a dimension H thereof as measured in a longitudinal direction Y, and the second breast milk absorbent pad 2(*ii*) is fed so as to be displaced from a transverse center line 32 toward an lower end 30 by ¼ of a dimension H thereof as measured in a longitudinal direction Y. In a third step, the first and second breast milk absorbent pads 2, 3(*iii*) are respectively folded back from the upper end and lower ends 30, 31 toward the transverse center line 32 in two-ply fashion. In a fourth step, the upper and lower ends of the wrapping sheet web 29 are folded back toward the transverse center line 32. In a fifth step, a joint zone 20 is formed between the first and second breast milk absorbent pads 2, 3(*v*) and these two pads 2, 3(*v*) is cut apart along a cutting line 33.

8 Claims, 6 Drawing Sheets

U.S. PATENT DOCUMENTS

| | | | |
|---|---|---|---|
| 5,879,500 A * | 3/1999 | Herrin et al. | 156/204 |
| 5,979,144 A * | 11/1999 | Bailey et al. | 53/413 |
| 6,115,997 A * | 9/2000 | Burrow et al. | 53/412 |
| 6,176,371 B1 * | 1/2001 | Tyrrell | 206/204 |
| 6,935,091 B2 * | 8/2005 | Gamberini | 53/466 |
| 6,978,584 B1 * | 12/2005 | Burrow et al. | 53/412 |
| 7,908,824 B2 * | 3/2011 | Kuroda et al. | 53/416 |
| 2005/0198931 A1 * | 9/2005 | Cesiro et al. | 53/461 |
| 2007/0099542 A1 | 5/2007 | Sakaguchi et al. | |
| 2008/0276570 A1 * | 11/2008 | Kuroda et al. | 53/412 |
| 2011/0017628 A1 * | 1/2011 | Oba et al. | 206/494 |
| 2011/0167765 A1 * | 7/2011 | Yamamoto | 53/429 |

FOREIGN PATENT DOCUMENTS

| | | |
|---|---|---|
| JP | 2000-247358 | 9/2000 |
| JP | 2000-309391 | 11/2000 |
| JP | 2001-088866 | 4/2001 |
| JP | 2002-362626 | 12/2002 |
| JP | 2003-013305 | 1/2003 |
| JP | 2007-126161 | 5/2007 |
| JP | 2007-326622 | 12/2007 |

* cited by examiner

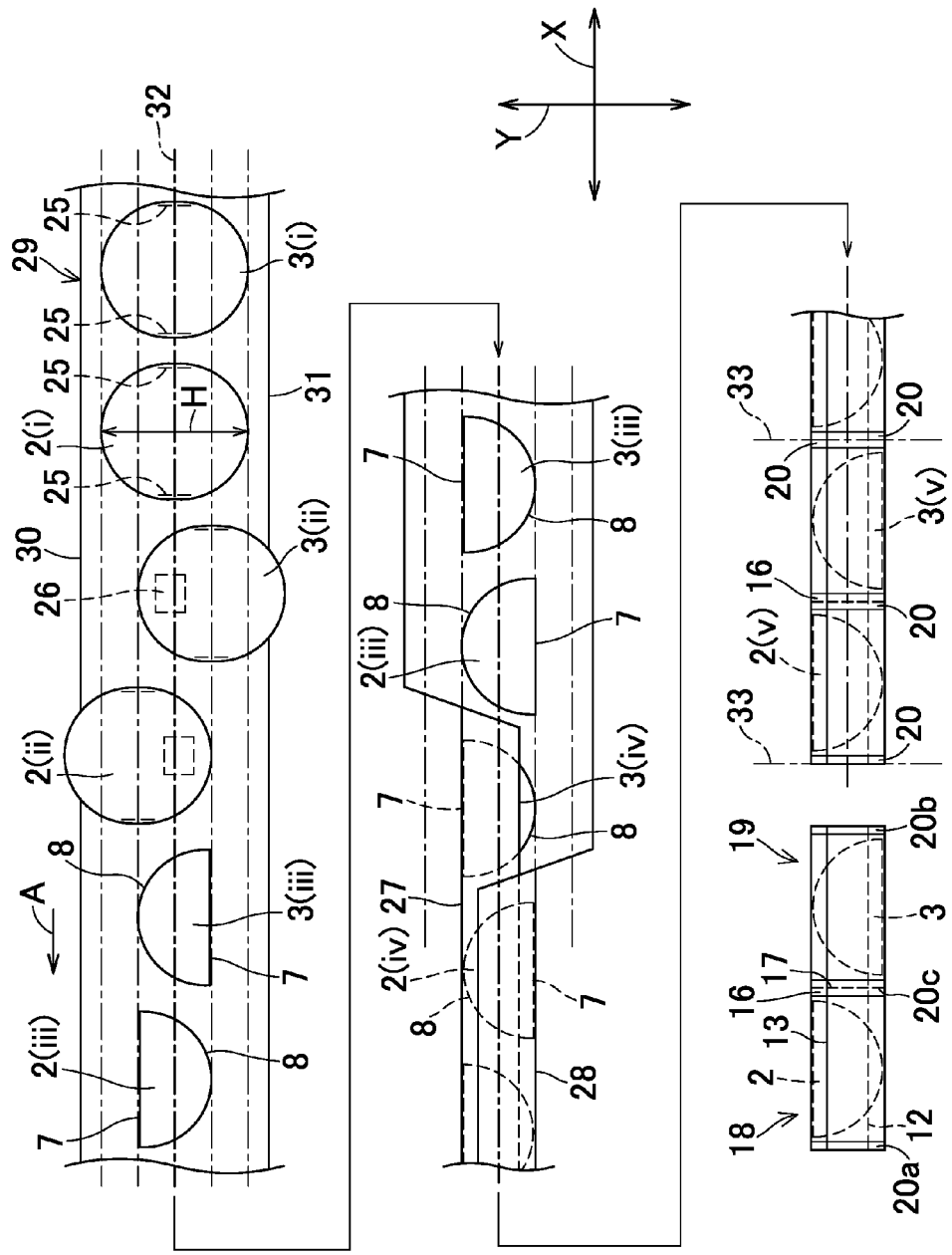

METHOD FOR MAKING PACKAGE-ABSORBENT ARTICLE ASSEMBLY AND PACKAGE-ABSORBENT ARTICLE ASSEMBLY OBTAINED BY THE SAME

RELATED APPLICATION

This application is a 35 U.S.C. §371 national phase filing of International Patent Application No. PCT/JP2008/071077, filed Nov. 11, 2008, through which and to which priority is claimed under 35 U.S.C. §119 to Japanese Patent Application No. 2008-008530, filed Jan. 17, 2008.

TECHNICAL FIELD

The present invention relates generally to a package-absorbent article assembly and a method for packaging such an article and more particularly to a packaged breast milk absorbent pad, a disposable diaper, a sanitary napkin, a panty liner or pad for hemorrhoidal patient, and a method for making the same.

RELATED ART

Conventionally package-absorbent article assemblies have been available for various purposes and in various forms. For example, JP2000-247358A discloses a package-breast milk absorbent pad assembly comprising a set of two pads adapted to be taken out from a single-purpose case when it is desired to use one or two pad. According the disclosure of this JP2000-247358A, these two pads are respectively folded in two so as to form an open edge and a closed edge, then these two pads are arranged so that the open edge of the one pad is opposed to the closed edge of the another pad, and these two pads are wrapped together with a wrapping sheet. The set of pads wrapped in this manner is now folded together with the wrapping sheet so that the pads are stacked upon each other. Plural sets of package-pad assemblies folded in this manner are packed in the case so that each set of two breast milk absorbent pads may be taken out from the case when it is desired to use one or two the pad. The steps of folding each of the pads and then folding the wrapped two pads so that the open edge of one pad overlaps the closed edge of another pad. Thereby not only thickness of the individual package-pad assembly but also total thickness of plural sets of the package-pad assemblies packed in the case can be maintained substantially uniform even if there is a differential thickness between the open edge and the closed edge. In an advantageous consequence, a plurality of the package-pad assemblies can be packed in the case with no space between each pair of the adjacent package-pad assemblies so far as the thickness of the individual set of package-pad subassemblies is substantially uniform.
Patent Document 1: JP2000-247358A

DISCLOSURE OF THE INVENTION

Problem to be Solved by the Invention

As long as a pair of the breast milk absorbent pads is packaged as unit set, when the user intends to use one of the pads alone, another pad becomes necessarily surplus. To properly use this surplus pad later, this surplus pad must be wrapped again with the wrapping sheet which has been once unfolded. Handling of rewrapping takes time and labor often with poor hygiene.

According to the method for making the package-breast milk absorbent pads assembly as described above, the pads are respectively folded in two and placed on the wrapping sheet and further folded together with the wrapping sheet. To prevent the respective pads once folded in two from being significantly unfolded before these pads respectively folded in two are folded together with the wrapping sheet so that the individual pads are stacked upon each other, it is required to fold the individual pads excessively acutely. However, such acutely folded pad often leaves a fold mark or crease and the pad becomes disadvantageously stiff along the fold line.

In view of the problem as has been described above, it is an object of the present invention to provide a package-absorbent article assembly and a method for making such assembly improved so that each set of two absorbent articles can be easily taken out from the case and, even when the user intends to use only one of these two absorbent article, the surplus one may be easily and hygienically stored for later use and, in addition, the absorbent article may be free from fold mark or crease left behind and/or free from becoming stiffness along the folding line.

Measure to Solve the Problem

According to one aspect of the present invention, there is provided a method for making a package-absorbent article assembly comprising an absorbent article packaged with a wrapping sheet wherein the absorbent article has a longitudinal direction and a transverse direction and comprises an inner sheet facing a user's body, an outer sheet facing the user's garment and a liquid-absorbent structure sandwiched between the inner and outer sheets.

This aspect of the present invention further comprising the steps of: using a first absorbent article and a second package-absorbent article as the package-absorbent article assembly alternately feeding the first and second absorbent articles at regular intervals onto a continuous wrapping sheet web along a center line extending in the transverse direction so as to bisect a dimension of the wrapping sheet web as measured between its upper and lower ends opposed to each other in the longitudinal direction and extending in the transverse direction, displacing the first absorbent article aside from the center line toward the upper end and displacing the second absorbent article aside from the center line toward the lower end, folding back the first absorbent article from the upper end toward the center line in a two-ply fashion, folding back said second absorbent article from the lower end toward the center line in a two-ply fashion, then folding back the upper end of the wrapping sheet web toward the center line along a fold line of the first absorbent article and folding back the lower end of the wrapping sheet web toward the center line along a fold line of the second absorbent article, bonding layers of the wrapping sheet web overlapping each other in a joint zone defined between each pair of the first absorbent article and the second absorbent article adjacent in the transverse direction, and cutting the wrapping sheet web substantially in a middle of the joint zone to obtain each set having a given number of pair of a first package-pad subassembly containing therein the first absorbent article and a second package-pad subassembly containing the second absorbent article.

According to one preferred embodiment of this aspect of the present invention, a dimension of the wrapping sheet web as measured in the longitudinal direction is substantially the same as a dimension of the first and second absorbent articles as measured in the longitudinal direction and the first and second absorbent articles are displaced from each other in the longitudinal direction by ¼ of the dimension as measured in the longitudinal direction.

According to another preferred embodiment of this aspect of the present invention, the wrapping sheet web is cut so as to obtain each set having one pair of the first package-absorbent article subassembly and the second package-absorbent article subassembly.

According to still another preferred embodiment of this aspect of the present invention, the upper end of the wrapping sheet web is folded back toward the center line and the lower end is folded back toward the center line so as to overlap the upper end substantially at the same time as the first absorbent article is folded back and thereby to obtain the first package-absorbent article subassembly. To obtain the second package-absorbent article subassembly, after the second absorbent article has been folded, the upper end is folded back toward the center line and the lower end is folded back toward the center line so as to overlap the upper end.

According to the other aspect of the present invention, there is provided a package-absorbent article assembly comprising: in that the absorbent article having a longitudinal direction and a transverse direction and comprising an inner sheet defining a side facing a user's skin, an outer sheet defining a side facing the user's garment, a liquid-absorbent structure sandwiched between the inner and outer sheets, a closed edge defined by a fold line along which the absorbent article is folded back in a two-ply fashion with the inner sheet inside so as to bisect its dimension in the longitudinal direction, and folded front and rear surfaces, the wrapping sheet having upper and lower ends opposed to each other in the longitudinal direction and extending in the transverse direction, a first section opposed to the outer sheet defining the front surface of the absorbent article having been folded back, a second section contiguous to the first section and opposed to the outer sheet defining the rear surface and a third section contiguous to the second section and overlapping the first section, wherein these first, second and third sections are joined together along outer sides of the absorbent article as viewed in the transverse direction by joint zones extending in the longitudinal direction.

Effect of the Invention

According to the present invention, feeding, folding, and wrapping with the wrapping sheet web of the first and second absorbent articles can be carried out by a series of steps and thereby a time loss can be reduced in comparison to the case in which the absorbent article is fed to the wrapping sheet web after the absorbent article has been folded back. A time taken from folding of the absorbent article to wrapping of this is sufficiently short to make it unnecessary to fold the absorbent article tightly and therefore a folded mark or crease would not be left on the article and/or the article would not be stiffened along the fold.

The first and second absorbent articles are continuously fed at regular intervals, then folded back in a two-ply fashion and wrapped with the wrapping sheet along the folded edges of the respective absorbent articles. It is also possible to wrap the first or second absorbent article one by one and, when only one absorbent article is used, the surplus absorbent article can be easily and hygienically stored for later use.

The first and second absorbent articles are arranged so as to be displaced from each other in the longitudinal direction by ¼ of the dimension of the wrapping sheet web as measured in the longitudinal direction. With such unique arrangement, the absorbent articles respectively folded back in a two-ply fashion may be wrapping sheet web folded back in a three-ply fashion to ensure that no space is left between the absorbent articles and the wrapping sheet web and the consumed quantity of the wrapping sheet web can be minimized. In consequence, the manufacturing cost can be correspondingly reduced.

The wrapping sheet web is cut to obtain each set having one pair of the first absorbent article and the second absorbent article to ensure that the article can be taken out from the case set by set and thereby time and labor can be saved in comparison to the case in which the article is taken out from the case one by one.

For the first package-pad subassembly, the first absorbent article and the wrapping sheet web may be folded substantially at once to eliminate a need for tightly folding the first absorbent article, on one hand, and to reduce a time taken for making the article.

BRIEF DESCRIPTION OF THE DRAWINGS

FIG. 5 Diagram schematically illustrating a method for making the package-pad assembly.

IDENTIFICATION OF REFERENCE NUMERALS USED IN THE DRAWINGS

Figure 1:
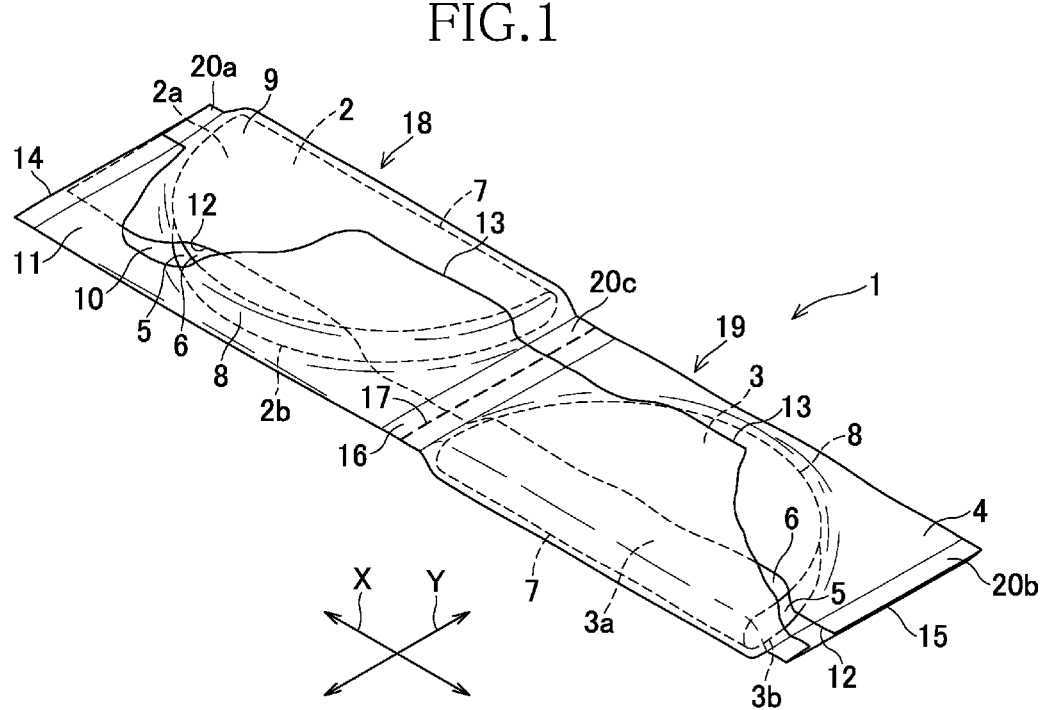
FIG. 1 Perspective view showing a package-pad assembly according to one embodiment of the invention.

1 package-pad assembly
2 first breast milk absorbent pad (first absorbent article)
3 second breast milk absorbent pad (second absorbent article)
4 wrapping sheet
5 inner sheet
6 outer sheet
9 first section
10 second section
11 third section
17 line of perforations
18 first package-pad subassembly
19 second package-pad subassembly
21 liquid-absorbent structure
29 wrapping sheet web
30 upper end
31 lower end
32 transverse center line Description Of The Best Mode For Working Of The Invention Details of the package-absorbent article assembly and the method for making the same according to the present invention will be more fully understood from the description given hereunder on the basis of a breast milk absorbent pad and the method for making such package-breast milk absorbent pad assembly in reference to the accompanying drawings.

EXAMPLE 1

FIG. 1 is a perspective view of a package-breast milk absorbent pad assembly 1 as partially cutaway for convenience of illustration.

The assembly according to this example comprises first and second breast milk absorbent pads 2, 3 arranged in a transverse direction X and a wrapping sheet 4 used to wrap these breast milk absorbent pads 2, 3. Each of the first and second breast milk absorbent pads 2, 3 comprises an inner sheet 5 facing a user's body, an outer sheet 6 facing the user's garment, wherein each of pads 2, 3 is folded in two and a dimension in the longitudinal direction Y is bisected. Each of the first and second breast milk absorbent pads folded in this manner has a closed edge 7 defined along fold and open edge 8 along which the respective halves of the pad are not contiguous to each other. The first and second breast milk absorbent pads 2, 3 folded in this manner respectively define front surfaces 2a, 3a extending on a side of this perspective view facing the viewer and rear surfaces 2b, 3b extending on a side of this perspective view facing away from the viewer.

The first and second breast milk absorbent pads 2, 3 are wrapped with a single continuous wrapping sheet 4. The wrapping sheet 4 is folded in a three-ply fashion so as to wrap the first and second breast milk absorbent pads 2, 3 and to form a first section 9, a second section 10 and a third section 11. The first section 9 includes one end 12 of the wrapping sheet 4 and partially covers the front surfaces 2a, 3a of the first and second breast milk absorbent pads 2, 3. The second section 10 is contiguous to the first section 9 and entirely covers the rear surfaces 2b, 3b. The third section 11 is contiguous to the second section 10 and includes the other end 13 of the wrapping sheet 4 so as to partially cover the front surfaces 2a, 3a. By overlapping the end 12 of the first section 9 and the end 13 of the third section 11 to each other, the front surfaces 2a, 3a are entirely covered with these layers 9, 11 and an outlet for the first and second breast milk absorbent pads 2, 3 is formed.

The wrapping sheet 4 comprises side edges 14, 15 opposed to each other in the transverse direction X and a middle region 16 extending substantially in a middle between the side edges 14, 15 so that the first and second breast milk absorbent pads 2, 3 are spaced from each other with interposition of the middle region 16 and in bilateral symmetric relationship about the middle region 16. In these side edges 14, 15 and the middle region 16, the first, second and third layer 9, 10, 11 are bonded one to another along joint zones 20a, 20b, 20c. The joint zones 20a, 20b, 20c are formed intermittently in the longitudinal direction Y. While heat sealing technique is used to form these joint zones according to the illustrated embodiment, it is also possible to form the joint zones by using any suitable adhesive and the other widely used means. The package-pad assembly 1 is divided and defined by the joint zone 20c formed in the middle region 16 into a first package-pad subassembly 18 enveloping the first breast milk absorbent pad and a second package-pad subassembly 19 enveloping the second breast milk absorbent pad.

The middle region 16 is formed with a line of perforations 17 extending in the longitudinal direction Y and substantially bisecting the joint zone 20c. The line of perforations 17 allows the package-pad assembly 1 to be severed into a first package-pad subassembly 18 enveloping therein the first breast milk absorbent pad 2 and a second package-pad subassembly 19 enveloping therein the second breast milk absorbent pad 3. The means allowing the package-pad assembly 1 to be severed into first package-pad subassembly 18 enveloping therein the first breast milk absorbent pad 2 and a second package-pad subassembly 19 enveloping therein the second breast milk absorbent pad 3 is not limited to the line of perforations and may be formed by the other widely used means. It should be appreciated that the joint zone 20c is preferably present on the sides of both the first package-pad subassembly 18 and the second package-pad subassembly 19.

Figure 2:
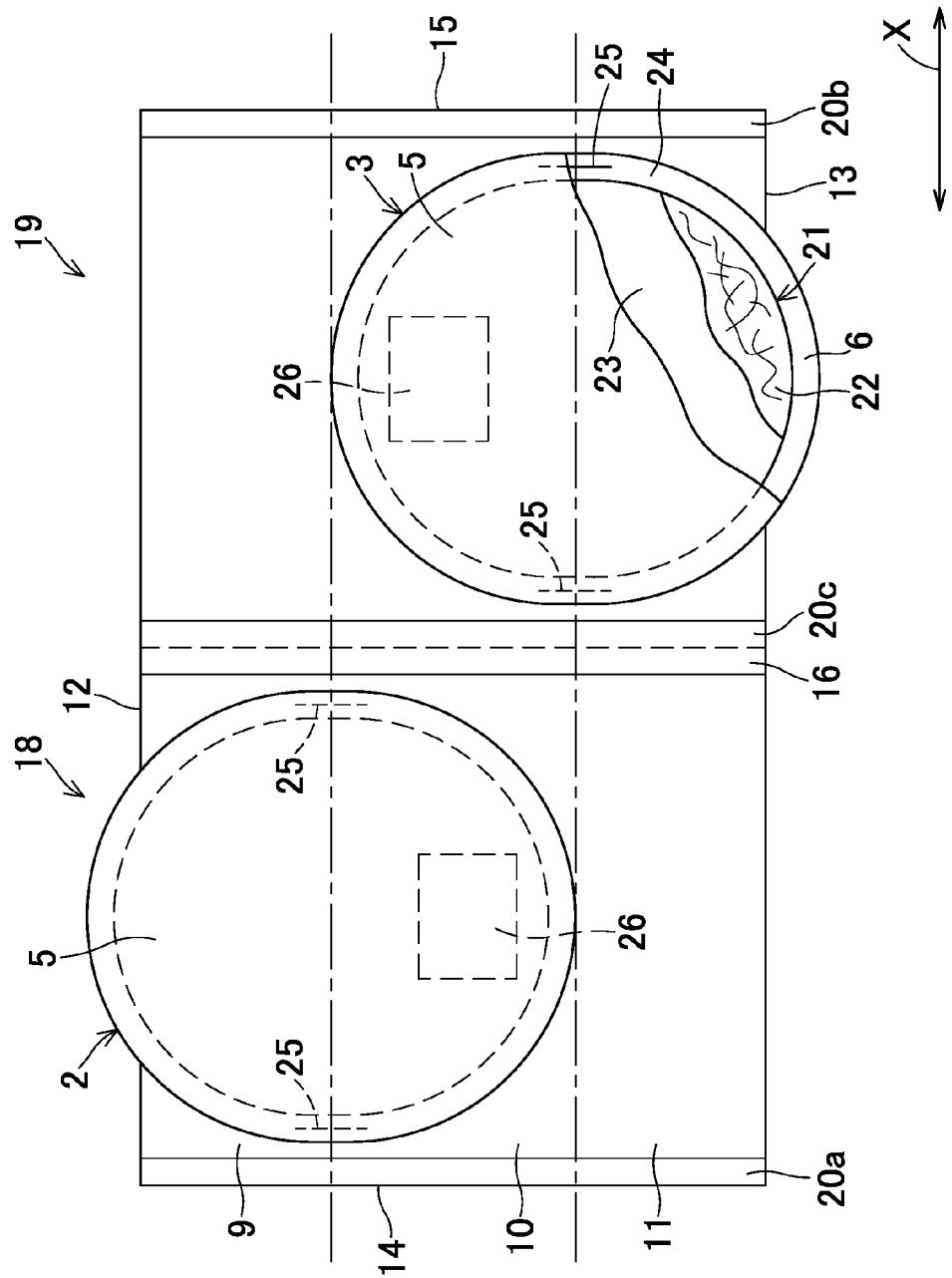
FIG. 2 Developed view corresponding to FIG. 1.

FIG. 2 is a developed view showing the package-pad assembly of FIG. 1 when the joint zones 20a, 20b, 20c formed along the side edges 14, 15 and the middle region 16, respectively have been destroyed. As shown, the first breast milk absorbent pad 2 is allocated so that this pad 2 partially overlaps the one end 12 included by the first section 9 and overlaps the first section 9 and the second section 10. The second breast milk absorbent pad 3 is allocated so that this pad 3 partially overlaps the other end 13 included by the third section 11 and overlaps the second section 10 and the third section 11. Specifically, the first breast milk absorbent pad 2 and the second breast milk absorbent pad 3 are displaced from each other in the longitudinal direction Y and substantially symmetric with respect to the transverse direction X.

Each of the first and second breast milk absorbent pads 2, 3 comprises the inner sheet 5 defining the side facing the user's skin, the outer sheet 6 defining the side facing the user's garment and a liquid-absorbent structure 21 sandwiched between the inner and outer sheets 5, 6. The liquid-absorbent structure 21 comprises a liquid-absorbent core 22 and a spreading sheet 23 with which the liquid-absorbent core 22 is wrapped. The inner and outer sheets 5, 6 are substantially circular and substantially isometric while the liquid-absorbent structure 21 is also substantially circular but slightly smaller than the inner and outer sheets 5, 6. The liquid-absorbent structure 21 and the inner and outer sheets 5, 6 are laminated one upon another so as to describe concentric circles wherein the inner and outer sheets 5, 6 are joined together along respective outer peripheries 24 of these inner and outer sheets 5, 6 in which the liquid-absorbent structure 21 is absent, by means of adhesion or sealing.

Each of the first and second breast milk absorbent pads 2, 3 is provided in lateral regions opposed to each other in the transverse direction X with elastic members 25 extending in the longitudinal direction Y and attached under tension to the respective pads 2, 3. Contraction of these elastic members 25 gives a three-dimensional appearance to the first and second breast milk absorbent pads 2, 3. Specifically, these pads 5, 6 become dome-shaped.

The first and second breast milk absorbent pads 2, 3 are bonded to the inner surface of the wrapping sheet 4 by the intermediary of release sheets 26. Each of the first and second breast milk absorbent pads 2, 3 is coated on its outer sheet 6 with adhesive (not shown) so that the outer sheet 6 may be releasably bonded to the associated release sheet 26. The release sheet 26 is permanently bonded to the section of the wrapping sheet 4 opposed to the outer sheet 6, i.e., to the second section 10 of the wrapping sheet 4 by adhesive (not shown).

Figure 3:
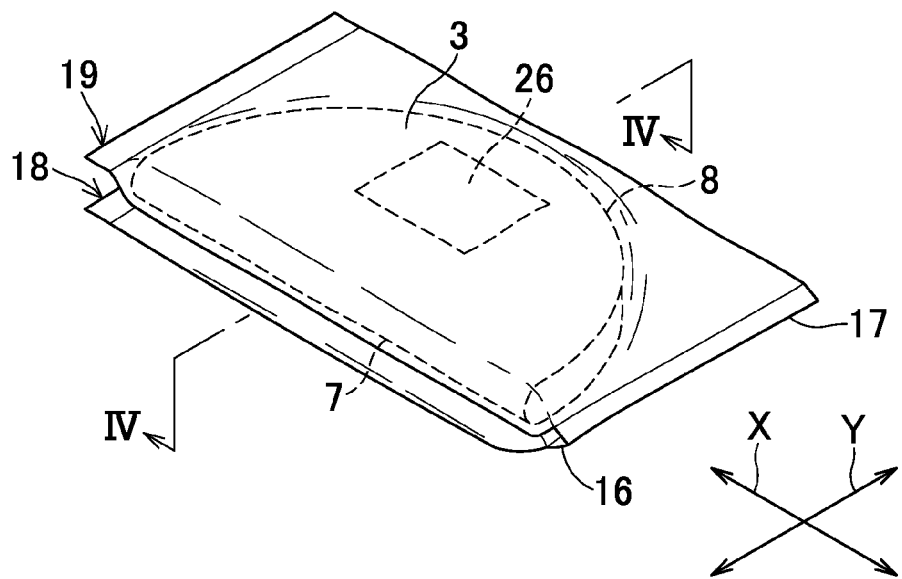
FIG. 3 Perspective view showing the package-pad assembly FIG. 1 in folded state.

The first and second package-pad assemblies 18, 19 enveloping therein the first and second breast milk absorbent pads 2, 3, respectively, are folded from the state of FIG. 1 to the state of FIG. 3. Specifically, the first and second package-pad assemblies 18, 19 are folded along the middle region 16 so that the respective third sections 11 of the wrapping sheet 4 are opposed to each other. Every set of the first and second package-pad assemblies 18, 19 held in such folded state to pack it in the case so as to be taken out from the case set by set when the user intends to use at least one of the first and second breast milk absorbent pads 2, 3.

Figure 4:
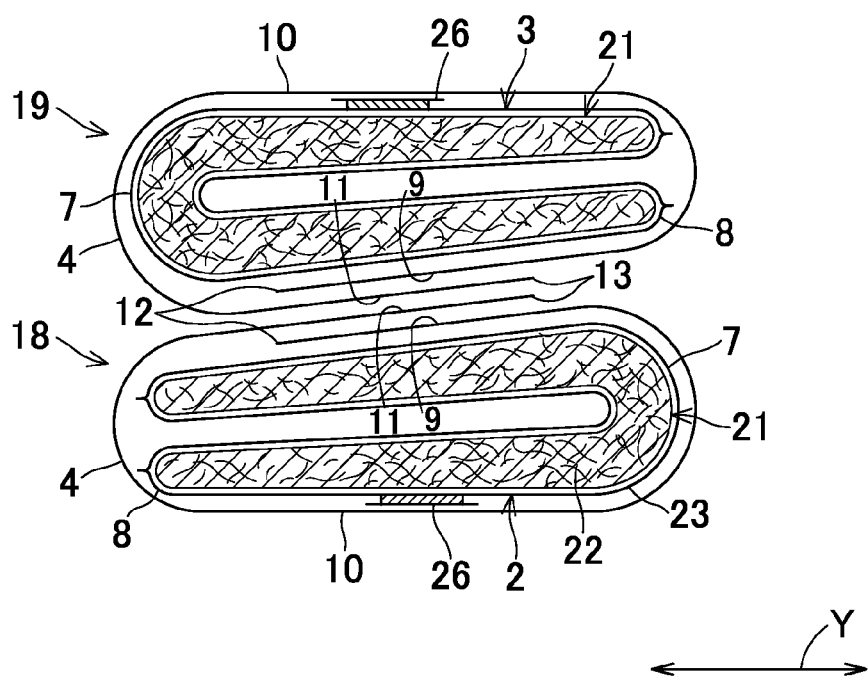
FIG. 4 Sectional view taken along the line IV-IV in FIG. 3.

FIG. 4 is a sectional view taken along the line IV-IV in FIG. 3. As will be apparent from FIG. 4, the second package-pad subassembly 19 overlies the first package-pad subassembly 18 as viewed in the thickness direction of the first package-pad subassembly 18. In the first package-pad subassembly 18, the closed edge 7 lies at a relatively high level (right side in FIG. 4) as viewed in the longitudinal direction Y and the open edge 8 lies at a relatively low level (left side in FIG. 4) as viewed in the longitudinal direction Y. This is for the reason that, in the first breast milk absorbent pad 2, the amount of the liquid-absorbent core 22 gradually decreases from the maximum in a central region toward the outer periphery 24 and consequently the thickness of the first breast milk absorbent pad 2 folded in two gradually decreases from the maximum along its closed edge 7 toward its open edge 8.

In the second package-pad subassembly 19, the open edge 8 of the second breast milk absorbent pad 3 lies at a relatively high level (right side in FIG. 4) as viewed in the longitudinal direction Y while the closed edge 7 lies at a relatively low level (left side in FIG. 4) as viewed in the longitudinal direction Y. The second breast milk absorbent pad 3 is similar to the first breast milk absorbent pad 2 so far as the construction is concerned and therefore the thickness of the second breast milk absorbent pad 3 also gradually decreases from the maximum along the closed edge 7 toward the open edge 8.

With the above-described first and second package-pad subassemblies 18, 19 folded as shown by FIG. 3, the closed edge 7 and the open edge 8 of the first breast milk absorbent pad 2 overlap the open edge 8 and the closed edge 7 of the second breast milk absorbent pad 3. Such overlapping in alternate fashion allows the set of the first and second breast milk absorbent pads 18, 19 folded in this manner to have a substantially uniform thickness. Plurality of such sets stacked in the thickness direction may be packed in the case. Even when a plurality of sets must be stacked, the stack packed in the case would not become partially thick since the individual set of the package-pad subassemblies has a uniform thickness. Thus a plurality of the sets can be packed in the case without any significant space between each pair of the adjacent sets.

When it is desired to take out the package-breast milk absorbent pad assembly from the case for actual use, any one of the first and second package-pad subassemblies 18, 19 being contiguous to each other at this time may be pinched by the fingers and pulled up to take out these two package-pad subassemblies 18, 19 from the case at once. These first and second package-pad subassemblies 18, 19 are detachably contiguous to each other along the line of perforations 17 provided in the middle region 16. Depending on the user's need, the first and second package-pad subassemblies 18, 19 may be separated along the line of perforations 17 to use only one of them. The other surplus breast milk absorbent pad may be stored in a packaged state, i.e., sanitarily for a later use.

When one of the first and second breast milk absorbent pads 2, 3 is used, the user may take out the breast milk absorbent pad 2 or 3 from the associated package-pad subassembly 18 or 19. Specifically, the end 13 on the side of the third section 11 may be held by the fingers and pulled apart from the first section 9 and the second section 10 (See FIG. 1). By pulling the end 13 in this manner, the joint zone 20 of the third section 11 is released and the end 12 is exposed.

Beyond the end 12, the open edge 8 of the first breast milk absorbent pad 2 or the closed edge 7 of the second breast milk absorbent pad 3 extends outward. The open edge 8 or the closed edge 7 may be held by the one hand and the end 12 may be held by the other hand to pull them apart from each other. In this way, the joint zones 20 on the first section 9 and the second section 10 are also released and thereby the breast milk absorbent pad may be peeled off from the wrapping sheet 4. The release sheet 26 remains bonded to the wrapping sheet 4 and the breast milk absorbent pad is detached from the release sheet 26. The region of the breast milk absorbent pad coated with adhesive which has been covered with the release sheet 26 is now exposed and can be utilized to fix the breast milk absorbent pad to the user's garment such as a brassiere.

FIG. 5 is a diagram schematically illustrating a method for making the first package-pad subassembly 18 and the second package-pad subassembly 19. The first and second breast milk absorbent pads 2, 3 are fed at regular intervals onto a continuous wrapping sheet web 29 and packaged as the wrapping sheet web 29 are folded. The wrapping sheet web 29 extending in the transverse direction X and is conveyed in a direction indicated by an arrow A by a conveyor belt (not shown). The wrapping sheet web 29 upper and lower ends 30, 31 opposed to each other in the longitudinal direction Y and extending in the transverse direction X and a transverse center line 32 extending in the transverse direction X so as to bisect a dimension between the upper and lower ends 30, 31. A dimension as measured from the upper end 30 to the lower end 31 of the wrapping sheet web 29 is set to be slightly larger than a dimension H of the respective breast milk absorbent pads 2, 3 in the longitudinal direction Y.

In a first step, the first and second breast milk absorbent pads 2(*i*), 3(*i*) are fed onto the wrapping sheet web 29 so that both lateral regions of the respective pads provided with the elastic members 25 are successively opposed to the similar lateral regions of the adjacent pads in the transverse direction X. When these pads 2(*i*), 3(*i*) are fed so that these lateral regions of the respective pads are successively opposed to similar lateral regions of the adjacent pads in the longitudinal direction Y, these breast milk absorbent pads 2(*i*), 3(*i*) may be turned by an angle of 90° C. before they are fed onto the wrapping sheet web 29.

In a second step, the first breast milk absorbent pad 2(*ii*) is fed so that the first breast milk absorbent pad 2(*ii*) may be displaced from the transverse center line 32 toward the upper end 30 by ¼ of the dimension H of this first breast milk absorbent pad 2(*ii*) as measured in the longitudinal direction Y. The second breast milk absorbent pad 3(*ii*) is fed so that the second breast milk absorbent pad 3(*ii*) may be displaced from the transverse center line 32 toward the lower end 31 by ¼ of the dimension H of this second breast milk absorbent pad 3(*ii*) as measured in the longitudinal direction Y. The first and second breast milk absorbent pads 2(*ii*), 3(*ii*) are same in shape as well as in size and therefore the distances by which these pads should be displaced from the transverse center line 32 are also the same. The first breast milk absorbent pad 2(*ii*) and the second breast milk absorbent pad 3(*ii*) are alternately fed to the wrapping sheet web 29. Consequently, the first and second breast milk absorbent pads 2, 3 describe a zigzag pattern.

The respective outer sheets 6 of the first and second breast milk absorbent pads 2, 3 are provided with pressure-sensitive adhesive zones by which the pad or pads may be temporarily fixed to the user's garment. The release sheets 26 are permanently bonded to the wrapping sheet web 29 by adhesive in order to protect said pressure-sensitive adhesive zones before use of the breast milk absorbent pads.

In a third step, the first breast milk absorbent pad 2(*iii*) displaced upward is now folded from its upper end 30 toward the transverse center line 32 in a two-ply fashion to form the closed edge 7 defined along the folding line and the open edge 8. The second breast milk absorbent pad 3(*iii*) displaced downward is now folded from the lower end 31 toward the transverse center line 32 in a two-ply fashion to form the closed edge 7 defined along the folding line and the open edge 8.

In a fourth step, the upper end 30 of the wrapping sheet web 29 is folded toward the transverse center line 32 together with the first breast milk absorbent pad 2(*iv*) to form a first folding line 27 extending along the closed edge 7. The wrapping sheet web 29 is folded from its lower end 31 toward the transverse center line 32 together with the second breast milk absorbent pad 3(*iv*) to form a second folding line 28 extending along the closed edge 7.

Figure 6A:
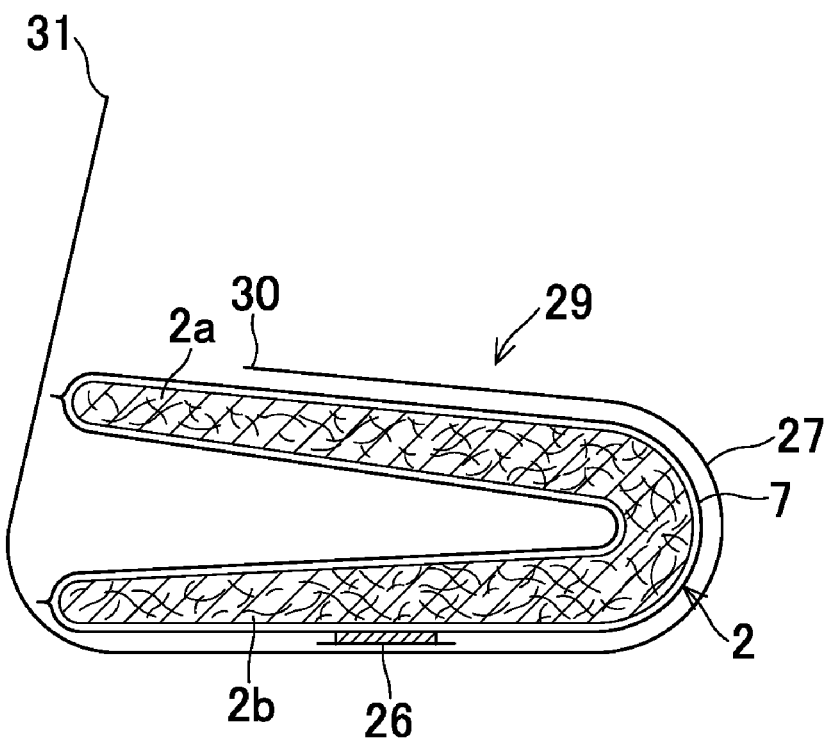
FIG. 6 Diagram schematically illustrating a method for making a first package-absorbent article subassembly.
Figure 6B:
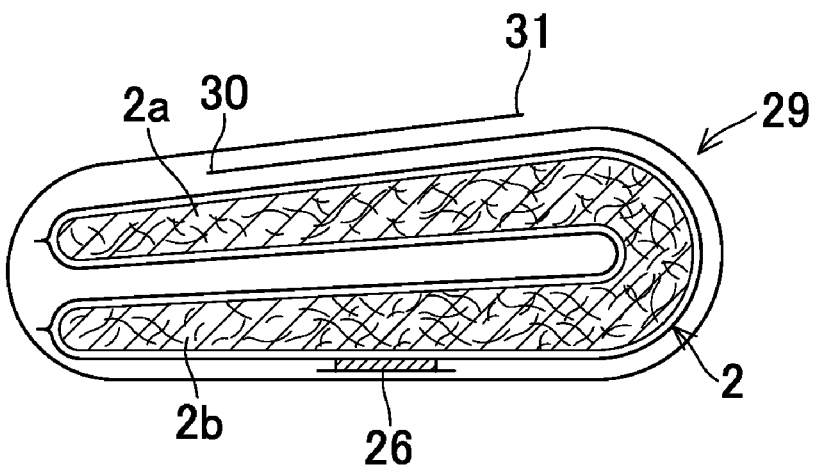

While it appears in the above-described third and fourth steps as if the process of folding the first and second breast milk absorbent pads 2(*iii*), 3(*iii*) and the process of folding the wrapping sheet web 29 would be separately carried out, these two processes may be carried out substantially at once. FIG. 6 illustrates a manner in which the first breast milk absorbent pad 2 is folded and this folded pad is wrapped with the wrapping sheet web 29. As will be apparent from FIG. 6A, the upper end 30 of the wrapping sheet web 29 is folded substantially at the same time as the first breast milk absorbent pad 2 is folded. Immediately after the first breast milk absorbent pad 2 and the upper end 30 of the wrapping sheet web 29 have been folded, the lower end 31 of the wrapping sheet web 29 is folded so as to overlap the upper end 30. In this way, the first breast milk absorbent pad 2 and the wrapping sheet web 29 may be folded substantially at once to reduce the number of steps and correspondingly to reduce the time required for manufacturing.

Figure 7A:
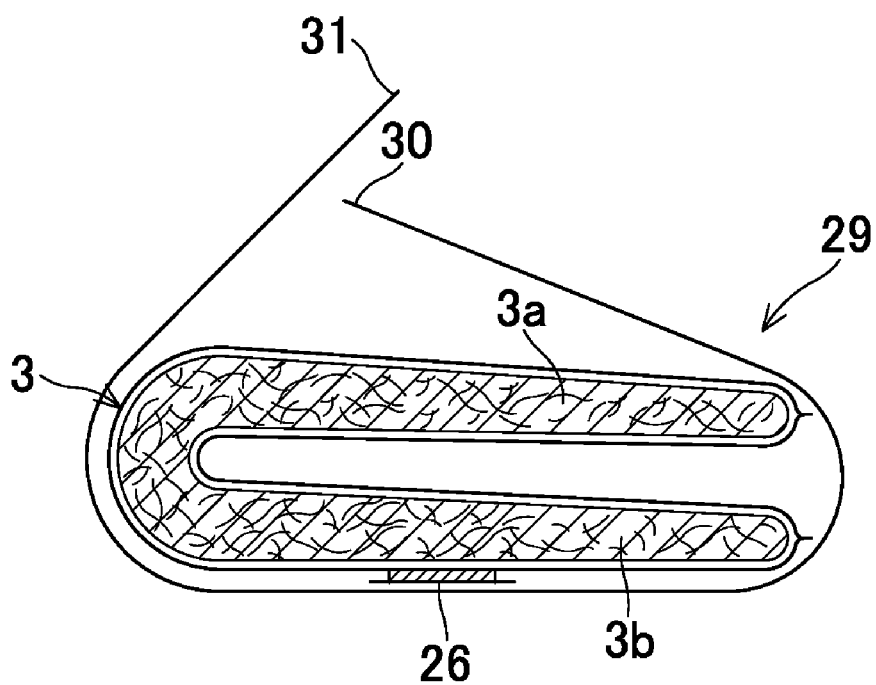
FIG. 7 Diagram schematically illustrating a method for making a second package-absorbent article subassembly.
Figure 7A:
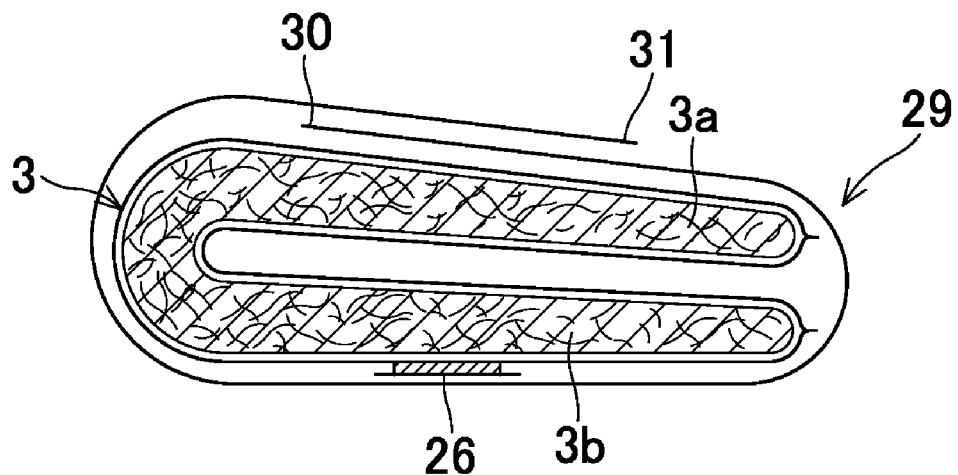

FIG. 7 illustrates a manner in which the second breast milk absorbent pad 3 is folded and this folded pad 3 is wrapped with the wrapping sheet web 29. Unlike the first breast milk absorbent pad 2 illustrated by FIG. 6, it is impossible here to fold the second breast milk absorbent pad 3 at the same time as the wrapping sheet web 29 is folded. In view of the fact that the upper end 30 of the wrapping sheet web 29 in FIG. 6 is contiguous to the upper end 30 of the wrapping sheet web 29 in FIG. 7, the upper end 30 of the wrapping sheet web 29 associated with the second breast milk absorbent pad 3 also will be folded as the upper end 30 of the wrapping sheet web 29 is folded in order to wrap the first breast milk absorbent pad 2. As a result, the upper end 30 of the wrapping sheet web 29 is folded ahead of the lower end 31 in association with both the first breast milk absorbent pad 2 and the second breast milk absorbent pad 3. To overcome this problem, the upper end 30 must be folded after the second breast milk absorbent pad 3 has been folded.

As illustrated in FIG. 7A, the second breast milk absorbent pad 3 is folded and then the upper end 30 of the wrapping sheet web 29 is folded back onto the front surface 3*a*. There is substantially no time lag between folding of the second breast milk absorbent pad 3 and folding of the wrapping sheet web 29 wherein the upper end 30 of the wrapping sheet web 29 is lapped on the second breast milk absorbent pad 3 so as to press the second breast milk absorbent pad 3 from its front surface 3*a*. After the upper end 30 has been folded in this manner, the lower end 31 of the wrapping sheet web 29 is folded back onto the upper end 30 as will be seen in FIG. 7B.

In a fifth step illustrated by FIG. 5, after the wrapping sheet web 29 has been folded, the joint zone 20 is formed between the first breast milk absorbent pad 2(*v*) and the second breast milk absorbent pad 3(*v*) and the folded wrapping sheet web 29 is heat sealed. Then, the assembly is cut along a cutting line 33 to obtain each set of the first breast milk absorbent pad 2(*v*) and the second breast milk absorbent pad 3(*v*). In addition, the line of perforations 17 is formed between the first breast milk absorbent pad 2(*v*) and the second breast milk absorbent pad 3(*v*).

By cutting the wrapping sheet web 29 containing therein the pads along the cutting line 33, the first package-pad subassembly 18 and the second package-pad subassembly 19 are obtained. The first and second package-pad subassemblies 18, 19 are detachably contiguous to each other so as to form one set. The cutting line 33 extends in the longitudinal direction Y substantially in the middle of the joint zone 20 as viewed in the transverse direction X. Cutting along the cutting line 33 divides the joint zone 20 into the joint zone 20*a* and the joint zone 20*b*. By cutting along the cutting lines 33, the wrapping sheet web 29 is divided into the individual wrapping sheets 4, the upper end 30 is divided into the one side ends 12 of the first and second package-pad subassemblies 18, 19, and the lower end 31 is divided into the other side ends 13 thereof.

According to the method as has been described above, immediately after or at the same time as the first and second breast milk absorbent pads 2, 3 have been or are folded, it is possible to wrap them with the wrapping sheet web 29. Therefore it unnecessary to tightly fold the first and second breast milk absorbent pads as the prior art has been the case. In consequence, a remarkable fold mark or crease would not be left on the breast milk absorbent pad or stiffening would not occur along the fold line. Thereby undesirable irritation of user's skin due to such crease and/or stiffening can be effectively alleviated. By folding the first breast milk absorbent pad 2 and the wrapping sheet web 29 substantially at once, a time loss from folding of the pad to wrapping this with the wrapping sheet web 29 can be reduced and the problems such as creasing and/or stiffening of the pad can be further reliably prevented. While it is not essential to fold the first breast milk absorbent pad 2 and the wrapping sheet web 29 substantially at once, it is desired to fold the wrapping sheet web 29 so as to restrain the folded breast milk absorbent pad being unfolded.

As will be apparent from FIG. 5, the first and second breast milk absorbent pads 2, 3 may be arranged to be displaced from each other in the longitudinal direction Y to ensure that the closed edge 7 of the first breast milk absorbent pad 2 and the open edge 8 of the second breast milk absorbent pad 3 lie substantially in a straight line in the transverse direction X when these pads 2, 3 are folded in two, respectively. With the first and second breast milk absorbent pads 2, 3 lying substantially in a straight line, the wrapping sheet web 29 may be folded in a three-ply fashion from the upper and lower ends 30, 31 to wrap the first and second breast milk absorbent pads 2, 3. In this state, the wrapping sheet web 29 comes in contact with the closed edge 7 and the open edge 8 of the first and second breast milk absorbent pads 2, 3 with substantially no space left the opposite ends in the longitudinal direction Y. As an advantageously result, the wrapping sheet web 29 can be used without waste and the cost can be correspondingly reduced.

The dimension of the wrapping sheet web 29 as measured in the longitudinal direction Y is set to be slightly larger than the dimension of the first and second breast milk absorbent pads 2, 3 as measured in the longitudinal direction Y. Therefore, the wrapping sheet web 29 may be folded in three-ply fashion to wrap the first and second breast milk absorbent pads 2, 3 and thereby to ensure that the upper and lower ends 30, 31 thereof overlap each other and reliably wrap these pads 2, 3. Alternatively, the dimension of the wrapping sheet web 29 as measured in the longitudinal direction Y may be same as the dimension of the first and second breast milk absorbent pads 2, 3 as measured in the longitudinal direction Y. In this case, the upper and lower ends 30, 31 of the wrapping sheet web 29 do not overlap each other when the wrapping sheet web 29 is folded along the first and second breast milk absorbent pads 2, 3 folded in a two-ply fashion. To compensate this, these upper and lower ends 30, 31 may be joined by suitable means such as adhesive tape. The length dimension of the wrapping sheet web 29 as measured in the longitudinal direction Y may be appropriately selected depending on various factors such as a thickness of the breast milk absorbent pad.

While the upper and lower ends 30, 31 overlapping each other are not bonded to each other as far as the illustrated embodiment is concerned, it is possible to bond these ends together in order to prevent the outlets of the first and second breast milk absorbent pads 2, 3 from being readily opened.

While the first package-pad subassembly 18 and the second package-pad subassembly 19 are detachably contiguous to each other by the intermediary of the line of perforations 17 according to the illustrated embodiment, these two subassemblies are initially separated from each other. Specifically, instead of providing the middle region 16 with the line of perforations 17, the first and second package-pad subassemblies 18, 19 may be cut off in the middle region 16 from each other so that the first and second breast milk absorbent pads 2, 3 may be taken out one by one for actual use. In this case, the first package-pad subassembly 18 or the second package-pad subassembly 19 constitutes each set. It is also possible to constitute each set of detachably contiguous one to another by three or more breast milk absorbent pads. The number of these pads may be appropriately selected.

The inner sheet 5 is preferably liquid-pervious and may be formed by, for example, nonwoven fabric modified to become hydrophilic. The outer sheet 6 is preferably liquid-impervious and may be formed by, for example, resinous film. The liquid-absorbent core 22 may comprise, for example, a mixture of fluff pulp and super-absorbent polymer particles, and the wrapping sheet 4 may be formed of, for example, a resinous film. For these components, various materials widely used the relevant technical field.

The invention claimed is:

1. A method for making a package-absorbent article assembly comprising: an absorbent article packaged with a wrapping sheet wherein said absorbent article has a longitudinal direction and a transverse direction and comprising an inner sheet facing a user's body, an outer sheet facing a user's garment and a liquid-absorbent structure sandwiched between said inner and outer sheets, wherein said method comprises the steps of:
   using a first absorbent article and a second absorbent article as said package-absorbent article assembly alternately feeding said first and second absorbent articles at regular intervals onto a continuous wrapping sheet web along a center line extending in said transverse direction so as to bisect a dimension of said wrapping sheet web as measured between its upper and lower ends opposed to each other in said longitudinal direction and extending in said transverse direction;
   displacing said first absorbent article aside from said center line toward said upper end and displacing said second absorbent article aside from said center line toward said lower end;
   folding back said first absorbent article from said upper end toward said center line in a two-ply fashion, folding back said second absorbent article from said lower end toward said center line in a two-ply fashion, then folding back said upper end of said wrapping sheet web toward said center line along a fold line of said first absorbent article and folding back said lower end of said wrapping sheet web toward said center line along a fold line of said second absorbent article;
   bonding two layers of said wrapping sheet web overlapping each other in a joint zone defined between each pair of said first absorbent article and said second absorbent article adjacent in said transverse direction; and
   cutting said wrapping sheet web substantially in a middle of said joint zone to obtain each set having a given number of pair of a first package-absorbent article subassembly containing therein said first absorbent article and a second package-absorbent article subassembly containing said second absorbent article.

2. The method for making said package-absorbent article assembly according to claim 1, wherein a dimension of said wrapping sheet web as measured in said longitudinal direction is substantially same as a dimension of said first and second absorbent articles as measured in said longitudinal direction and said first and second absorbent articles are displaced from each other in said longitudinal direction by one-fourth of said dimension of said first and second absorbent articles as measured in said longitudinal direction.

3. The method for making said package-absorbent article assembly according to claim 2, wherein said wrapping sheet web is cut so as to obtain each set having one pair of said first package-absorbent article subassembly and second package-absorbent article subassembly.

4. The method for making said package-absorbent article assembly according to claim 3, wherein:
   said upper end of said wrapping sheet web is folded back toward said center line and said lower end is folded back toward said center line so as to overlap said upper end substantially at the same time as said first absorbent article is folded back and thereby to obtain said first package-absorbent article subassembly; and
   after said second absorbent article has been folded, said upper end is folded back toward said center line and said lower end is folded back toward said center line so as to overlap said upper end and thereby to obtain said second package-absorbent article subassembly.

5. The method for making said package-absorbent article assembly according to claim 2, wherein:
   said upper end of said wrapping sheet web is folded back toward said center line and said lower end is folded back toward said center line so as to overlap said upper end substantially at the same time as said first absorbent article is folded back and thereby to obtain said first package-absorbent article subassembly; and
   after said second absorbent article has been folded, said upper end is folded back toward said center line and said lower end is folded back toward said center line so as to overlap said upper end and thereby to obtain said second package-absorbent article subassembly.

6. The method for making said package-absorbent article assembly according to claim 1, wherein said wrapping sheet web is cut so as to obtain each set having one pair of said first package-absorbent article subassembly and second package-absorbent article subassembly.

7. The method for making said package-absorbent article assembly according to claim 6, wherein:
   said upper end of said wrapping sheet web is folded back toward said center line and said lower end is folded back toward said center line so as to overlap said upper end substantially at the same time as said first absorbent article is folded back and thereby to obtain said first package-absorbent article subassembly; and
   after said second absorbent article has been folded, said upper end is folded back toward said center line and said lower end is folded back toward said center line so as to overlap said upper end and thereby to obtain said second package-absorbent article subassembly.

8. The method for making said package-absorbent article assembly according claim 1, wherein:

said upper end of said wrapping sheet web is folded back toward said center line and said lower end is folded back toward said center line so as to overlap said upper end substantially at the same time as said first absorbent article is folded back and thereby to obtain said first package-absorbent article subassembly; and after said second absorbent article has been folded, said upper end is folded back toward said center line and said lower end is folded back toward said center line so as to overlap said upper end and thereby to obtain said second package-absorbent article subassembly.

\* \* \* \* \*